United States Patent [19]
Alfery

[11] Patent Number: 5,655,519
[45] Date of Patent: Aug. 12, 1997

[54] PATIENT AIRWAY BITE BLOCK

[76] Inventor: David D. Alfery, 5543 S. Stanford Dr., Nashville, Tenn. 37215

[21] Appl. No.: 557,235

[22] Filed: Nov. 14, 1995

[51] Int. Cl.⁶ .......................... A61M 16/01; A61C 8/00
[52] U.S. Cl. .................. 128/200.26; 128/200.24; 128/201.26; 128/206.29; 128/207.14
[58] Field of Search .............. 128/200.14, 200.24, 128/201.26, 861, 206.29, 200.26, 207.14; 433/91, 93, 94, 140

[56] References Cited

U.S. PATENT DOCUMENTS

| | | | |
|---|---|---|---|
| 1,498,219 | 6/1924 | Williams | 600/237 |
| 1,500,107 | 7/1924 | Chandler | 128/200.14 |
| 2,172,998 | 9/1939 | Grout et al. | 601/139 |
| 2,694,397 | 11/1954 | Herms | 128/861 |
| 2,708,931 | 5/1955 | Freedland | 128/861 |
| 3,407,809 | 10/1968 | Ross | 128/861 |
| 4,167,814 | 9/1979 | Schubert | 433/93 |
| 4,425,911 | 1/1984 | Luomanen et al. | 128/200.26 |
| 4,975,057 | 12/1990 | Dyfvermark | 433/91 |
| 5,009,595 | 4/1991 | Osborn | 433/140 |
| 5,018,967 | 5/1991 | Schwalbach | 433/94 |
| 5,117,816 | 6/1992 | Shapiro et al. | 128/200.24 |
| 5,174,284 | 12/1992 | Jackson | 128/200.26 |

Primary Examiner—V. Millin
Assistant Examiner—V. Srivastava
Attorney, Agent, or Firm—Sughrue, Mion, Zinn, Macpeak & Seas

[57] ABSTRACT

A patient airway bite block which can be used together with laryngeal mask airways (LMAs), oral endotracheal tubes, and similar patient airways. The bite block includes a bite block portion which is wedge-shaped and defines a posterior portion and an anterior portion and has upper and lower non-incisor teeth engagement surfaces. The wedge-shaped bite block portion is angled such that the non-incisor teeth engagement surfaces gradually become farther apart in a direction from the posterior portion toward the anterior portion, thereby to hold a patient's incisors apart when the bite block is positioned in the patient's mouth at one side thereof. At least one pair of spaced apart flanges is provided. The flanges extend from the bite block portion and are dimensioned to be positioned between the patient's non-incisor teeth and cheek and on the tongue side of the patient's non-incisor teeth, respectively. The flanges serve to retain the bite block in place in the patient's mouth. A handle, for positioning the bite block within the patient's mouth and for removing the bite block therefrom, is fixedly attached to the bite block portion and operative to extend outside of the patient's mouth when the bite block is positioned in the patient's mouth.

33 Claims, 3 Drawing Sheets

PATIENT AIRWAY BITE BLOCK

BACKGROUND OF THE INVENTION

My invention relates to a patient airway bite block and, more particularly, to a bite block used together with laryngeal mask airways (LMAs), oral endotracheal tubes, and similar patient airways.

In general, patients undergoing general anesthesia must have their airways secured in order to assure adequate ventilation. This is often accomplished through the use of an LMA which functions in place of either a patient face mask or an endotracheal tube. LMAs are comprised of a distal portion which is a cuffed disc-like device which fits around the larynx in the posterior hypopharynx and a more proximal portion which is analogous to an endotracheal tube. LMAs are placed in anesthetized patients blindly and the exiting tube portion is positioned directly in the mid-line of the mouth.

Use of an LMA in anesthetized patients poses several serious problems. First, patients may bite down on the tube portion of the device and cause airway obstruction. This can lead very quickly to hypoxemia (i.e., dangerously low levels of oxygen in the blood) of the patient. Second, such biting by the patient's incisors can cause actual severing of the LMA and subsequent loss of control of the airway. Third, secretions tend to accumulate in the back of the throat during general anesthesia because there is a loss of the normal swallowing reflexes in anesthetized patients. In a lightly anesthetized patient, or in a patent that is awakening from general anesthesia, such secretions can cause laryngospasm and subsequent airway closure. The reason that the secretions cause such a reaction is because the airway reflexes are heightened during light stages of general anesthesia. In order to treat laryngospasm, practitioners must use positive pressure ventilation and occasionally are forced to temporarily paralyze patients using neuromuscular blocking drugs. The practitioner can minimize the likelihood of experiencing laryngospasm by suctioning the secretions from the hypopharynx. Because of the above-described problems encountered using an LMA, it is necessary to place a bite block between the teeth of the anesthetized patient.

Conventionally, practitioners have relied on "homemade" solutions to the problem of utilizing a bite block with LMAs. Moreover, bite blocks designed for use with dental patients are inappropriate for use with LMAs because there is no handle attached. If an ordinary bite block is used in anesthetized patients, it could fall into the back of the throat and either cause airway obstruction when the LMA is removed, or be carried into the esophagus and alimentary tract. In addition, since conventional dental bite blocks are made for use in awake patients, they are not strong enough to withstand the tremendous forces which anesthetized patients generate when they involuntarily clench their teeth together.

Conventional oral airways which are used in patients anesthetized with their airway secured with oral endotracheal tubes are likewise not suitable for use with LMAs because such devices seat themselves directly in the mid-line of the mouth and thus compete for the space where the tube portion of the LMA exits the mouth. In addition, the posterior portion of the oral airway which is used to hold the tongue forward when used with an endotracheal tube impinges on the cuffed portion of the LMA in the hypopharynx and thereby cannot function properly.

Among the solutions practitioners have employed to provide bite blocks for patients with LMAs include the modification of other products which are intended for completely different uses. For example, a bite guard for use with gastroscopy patients has been described for use as a bite block. This device is not suitable because (1) it is not designed for use with LMAs and is not sized appropriately, (2) it is a non-disposable item and introduces the problem of the cost of cleaning and possible contamination to other patients, (3) it seats in the center of the mouth, (4) it is not safe for patients with frontal dental bridge work since this is the area that will bite down on the device, and (5) it has no handle and therefore can be easily lost in the back of the patient's throat. Other practitioners have tried to make bite blocks by wrapping gauze over the end of a tongue blade and holding the gauze in place with tape. This likewise is an unsatisfactory solution because of (1) the time required to assemble the device, (2) the difficulty in judging in the appropriate size required for any given patient, (3) the fact that the gauze can easily slip off the end of the tongue blade and be lost in the posterior hypopharynx, and (4) the wooden part of the tongue blade is easily broken.

An alternative to utilizing an LMA to secure the airway in an anesthetized patient is the use of an oral endotracheal tube. These patients also require a device which prevents occlusion or severing of the tube by the patient's incisors, and this is often accomplished by the use of a conventional oral airway. However, in patients who have oral endotracheal tubes in place and also have loose or fragile anterior dental work or loose incisors, biting down on an oral airway can cause damage to such anterior dental structures.

U.S. Pat. No. 4,425,911 (Luomanen et al.) discloses a bite-block for intubated endotracheal tubes. The bite block includes a body having a substantially rectangular cross-section, a face plate joined to the body at the exterior end thereof, and a projection extending laterally from the body on one side thereof. The body is provided with a longitudinally extending centrally located U-shaped channel open at the top, and a pair of continuously extending open-sided U-shaped channels on either side of the center channel. Upper and lower surfaces of the projection extend substantially perpendicular to the side of the main body, with the projection terminating in a flange. Ridges or steps are provided on the upper and lower surfaces and are configured for complementary engagement with the patient's canines, bicuspids and molars.

However, there are a number of drawbacks in the bite block of Luomanen et al. In particular, the upper and lower teeth contacting surfaces are not angled to provide for the jaw to be opened as wide as possible. For this reason, the Luomanen et al. bite block could not function to aid in LMA insertion. Moreover, the face plate of the Luomanen et al. device provides the potential for injury or damage to the incisors or lips by, for example, pressure exerted on the face plate causing the device to be pushed posteriorly and in turn easily damaging the incisors. The face plate also prevents further posterior movement of the device. Further still, the Luomanen et al. device is designed to hold an endotracheal tube precisely and tightly in place, whereas the LMA breathing tube portion requires a slight freedom of movement in order to perform adjustments in the cuff volume thereof. The Luomanen et al. device includes an integral portion designed to keep the tongue from slipping back into the patient's throat. Accordingly, as a patient awakens from a general anesthetic, the device must be removed prior to the return of the pharyngeal reflexes (i.e., gagging, regurgitation, etc.). The Luomanen et al. device lacks any type of handle for positioning and removing the device within and from, respectively, the patient's mouth.

U.S. Pat. No. 2,708,931 (Freedland) and U.S. Pat. No. 2,694,397 (Herms) disclose a mouth guard and a mouth prop, respectively, for patients undergoing shock therapy, epileptics, or other convulsive condition. However, such devices are unsuitable for use with LMAs because they are bilateral in configuration and therefore partly occupy the center of the mouth which would preclude the use of an airway product such as an LMA in conjunction therewith. Moreover, both of the devices are reusable and include handles which are positioned directly in a mid-line location that would interfere with a device such as an LMA. Also, with respect to the portion actually engaged by the patient's teeth, there is no angulation to provide for progressive opening of the jaw.

U.S. Pat. No. 5,009,595 (Osborn) discloses a mouth prop for dental patients. The device includes lateral flanges which keep the device from moving medially in the mouth. The flanges are molded specifically at a right angle from the bite block itself and thus are not angled away from the gum area. Furthermore, there are no flanges on the lingual (tongue) side so that a dentist can work on the medial aspects of the teeth in the area of the mouth prop. A hole is formed so that the practitioner can place dental floss or a cord through the device as a safety feature so as not to loose the device into the back of the patient's throat.

U.S. Pat. No. 5,174,284 (Jackson) discloses a bite block which is used specifically in awake or sedated patients undergoing endoscopic procedures such as gastroscopy. The bite block covers virtually the entire mouth and thus would be totally unsuitable for use with an LMA.

U.S. Pat. No. 1,498,219 (Williams) and U.S. Pat. No. 2,172,998 (Grout et al.) are cited simply to show a mouth prop for dentists and a gum massager, respectively.

SUMMARY OF THE INVENTION

My invention provides a bite block which overcomes the above-discussed drawbacks of the conventional devices. More specifically, my invention provides a disposable bite block, preferably for use with laryngeal mask airways (LMAs) or oral endotracheal tubes.

In accordance with my invention, a bite block is provided for use by a human patient and comprises a bite block portion defining a posterior portion and an anterior portion and having upper and lower non-incisor teeth engagement surfaces for engaging the patient's upper and lower non-incisor teeth in either side of the patient's mouth, thereby to hold the patient's incisors apart when said bite block is positioned in the patient's mouth at one side thereof. Upper and lower lateral flanges extend from the bite block portion and prevent the bite block from moving medially toward the patient's tongue, and upper and lower medial flanges spaced apart from the upper and lower lateral flanges, respectively, extend from the bite block portion and prevent the bite block from moving laterally toward the patient's cheek. A handle, for positioning the bite block within the patient's mouth and for removing the bite block therefrom, is fixedly attached to the bite block portion and is operative to extend outside of the patent's mouth when the bite block is positioned in the patient's mouth.

My invention further provides a disposable bite block which comprises a bite block portion which is wedge-shaped and defines a posterior portion and an anterior portion and has upper and lower non-incisor teeth engagement surfaces. The wedge-shaped bite block portion is angled such that the non-incisor teeth engagement surfaces gradually become farther apart in a direction from the posterior portion toward the anterior portion, thereby to hold the patient's incisors apart when the bite block is positioned in the patient's mouth at one side thereof. The bite block further comprises at least one pair of spaced apart flanges extending from the bite block portion and dimensioned to be positioned between the patient's non-incisor teeth and cheek and on the tongue side of the patient's non-incisor teeth, respectively. The pair of spaced apart flanges serve to retain the bite block in place. Further, the bite block includes a handle, for positioning the bite block within the patient's mouth and for removing the bite block therefrom, fixedly attached to the bite block portion and operative to extend outside of the patient's mouth when the bite block is positioned in the patient's mouth.

My invention still further provides a patient airway bite block for use with a patient airway including one of a laryngeal mask airway and an oral endotracheal tube, the patient airway having an exiting tube portion positioned in the mid-line of a patient's mouth. The patient airway bite block comprises a bite block portion which is wedge-shaped and defines a posterior portion and an anterior portion and has upper and lower non-incisor teeth engagement surfaces, the wedge-shaped bite block portion being angled such that the non-incisor teeth engagement surfaces gradually become farther apart in a direction from the posterior portion toward the anterior portion, thereby to hold the patient's incisors apart when the bite block is positioned in the patient's mouth at one side thereof and thus prevent the patient from biting down on the exiting tube portion of the patient airway. At least one pair of spaced apart flanges extend from the bite block portion and are dimensioned to be positioned between the patient's non-incisor teeth and cheek and on the tongue side of the patient's non-incisor teeth, respectively, the at least one pair of spaced apart flanges serving to retain the bite block in place in the patient's mouth. A handle, for positioning the bite block within the patient's mouth and for removing the bite block therefrom, is fixedly attached to the bite block portion and is operative to extend outside of the patient's mouth when the bite block is positioned in the patient's mouth.

The angle of the bite block is made according to the size of the accompanying LMA (or other substitute airway product such as an oral endotracheal tube) that the device is employed with. Accordingly, the practitioner is assured that the incisors of the patient are prevented from occluding or severing the breathing tube portion of the LMA or the like.

BRIEF DESCRIPTION OF THE DRAWINGS

Other features and advantages of the invention will be apparent from the following description taken in connection with the accompanying drawings, wherein.

DETAILED DESCRIPTION OF THE PREFERRED EMBODIMENTS

The invention will now be described with reference to the drawings.

Figure 1:
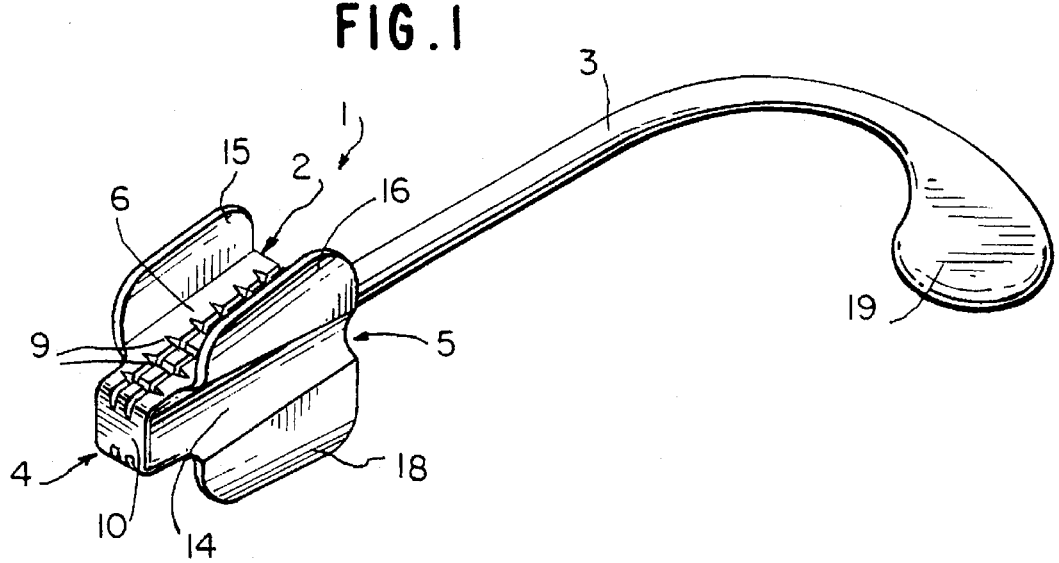
FIG. 1 is a perspective view of the bite block according to the present invention.

In FIG. 1, the bite block is generally denoted by the reference numeral 1. The bite block 1 is preferably formed of molded, medical grade plastic or other similarly hard material. The bite block 1 comprises a specialized bite block portion 2 with a fixedly attached handle 3. In general, the bite block is designed to be placed between the molar teeth on either side of the mouth thereby to hold the teeth apart (see FIGS. 7 and 8).

Figure 2:
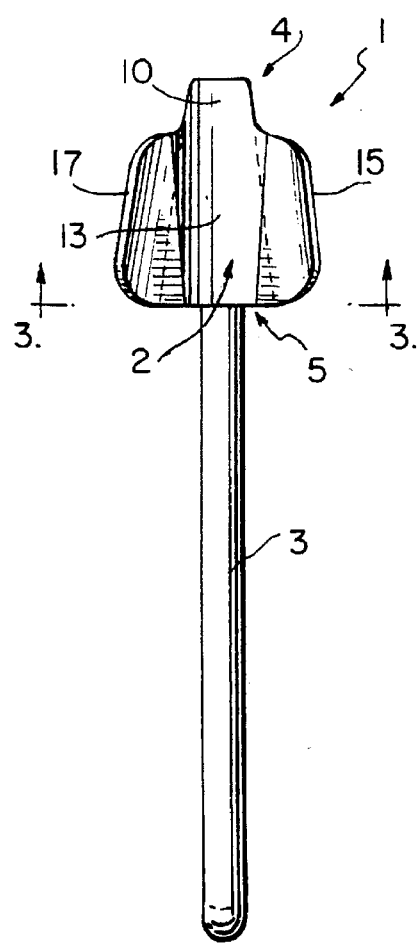
FIG. 2 is a side elevational view of the bite block according to the present invention.
Figure 7:
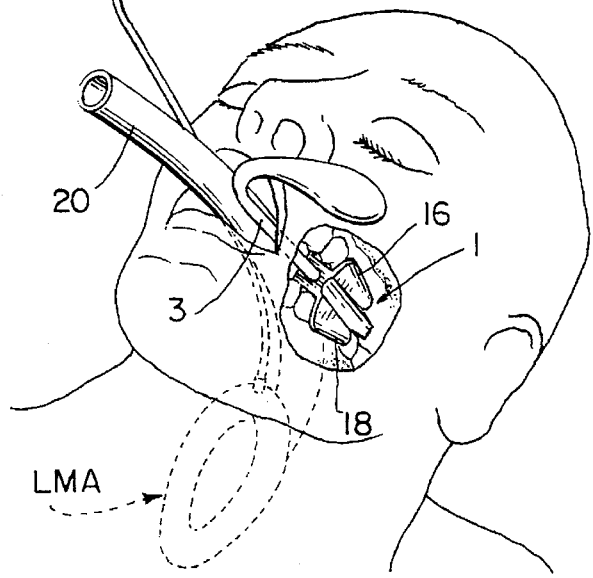
FIG. 7 is a schematic drawing showing the bite block according to the present invention used together with an LMA.

The bite block portion 2 is preferably wedge-shaped and defines a posterior portion 4 and an anterior portion 5. The bite block portion 2 further includes an upper non-incisor teeth engagement surface 6 and a lower non-incisor teeth engagement surface 7 (see FIG. 3). The wedge-shaped bite block portion 2 is angled such that the non-incisor teeth engagement surfaces 6 and 7 gradually become farther apart in the direction from the posterior portion 4 toward the anterior portion 5 as best seen in FIGS. 1 and 2. As a result, as the bite block portion 2 is inserted into the mouth between the non-incisor teeth of the patient, the patient's incisors are held apart when the bite block is fully positioned in the patient's mouth. The angle of the wedge-shaped bite block portion 2 is made according to the size of the accompanying LMA (or other substituted airway product such as an oral endotracheal tube—FIG. 8). In this way, the practitioner is assured that the incisors of the patient are prevented from occluding or severing the breathing or exiting tube portion 20 of the LMA as shown in FIG. 7.

Figure 4:
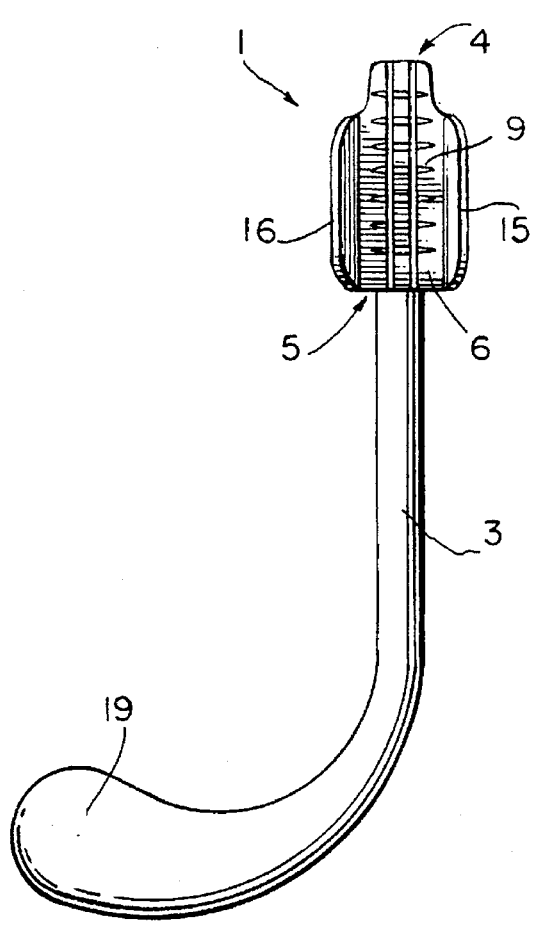
FIG. 4 is a top view of the bite block according to the present invention.

While the non-incisor teeth engagement surfaces 6 and 7 preferably engage the molar teeth of the patient, they are not limited to engagement with only such teeth but may also include engagement with the canine or bicuspid teeth. As shown in FIGS. 1 and 4, the non-incisor teeth engagement surfaces 6 and 7 may be formed so as to be serrated and irregular as at 9 in order to allow the ridges of the molars to seat onto the bite block in the optimal manner. In the preferred embodiment, the serrations 9 are in line with and horizontal to the bite block. However, other embodiments may equally be employed such as diagonal serrations, punctate holes, or still other irregular patterns on the non-incisor teeth engagement surfaces 6 and 7. Further still, the non-incisor teeth engagement surfaces 6 and 7 may take the form of a pliable surface such that the molars can grip the bite block portion 2.

Figure 3:
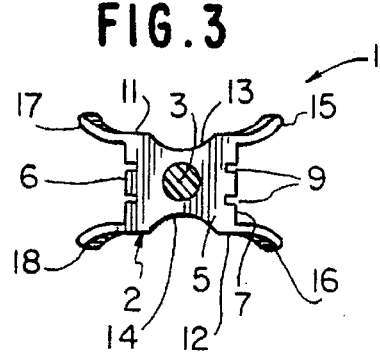
FIG. 3 is a cross-sectional view through the bite block taken along the lines 3—3 in FIG. 2.

A pair of spaced apart upper flanges 15 and 16 extend from an upper side of the bite block portion on the medial and lateral borders thereof, respectively, and a pair of spaced apart lower flanges 17 and 18 likewise extend from a lower side of the bite block portion on the medial and lateral borders of the bite block portion 2, respectively. The four flanges 15–18 together function to retain the bite block 1 in place within the patient's mouth. It should be understood that the designations "upper" and "lower" when describing the non-incisor teeth engagement surfaces 6 and 7 and the flanges 15–18 are simply for understanding the drawings, since the bite block can be rotated 180° as explained later on. The upper and lower lateral flanges 16 and 18 are dimensioned to be positioned between the patient's non-incisor teeth and cheek and specifically prevent movement of the bite block 1 towards the tongue, whereas the upper and lower medial flanges 15 and 17 are located on the tongue side of the patient's non-incisor teeth and function to prevent movement of the bite block 1 toward the patient's cheek. The upper and lower medial flanges 15 and 17 also serve to prevent the patient's tongue from being bitten between the bite block 1 and the non-incisor teeth, while the upper and lower lateral flanges 16 and 18 prevent the patient from biting the mucosa of the cheek. As best shown in FIG. 3, the distal portions or free ends of the pair of upper flanges 15 and 16 and the pair of lower flanges 17 and 18 are angled away from the bite block portion 2, and therefore away from the non-incisor teeth, in order to prevent the flanges from irritating the gums and alveolar ridges.

The bite block portion 2 further includes a projection 10 on the posterior portion 4 which extends beyond the four flanges 15–18 and which serves to prevent the bite block 1 from moving too far back in the mouth.

On opposite side walls 11 and 12 of the bite block 1, approximately at the midpoint between the upper and lower flanges, a molded groove 13, 14 is formed for permitting a suction catheter to pass into the posterior oropharynx. The grooves 13 and 14, in the present embodiment, are formed so as to be wider and deeper in the posterior portion 4 of the bite block portion 2 so as to allow a maximal area for suctioning on either side of the oropharynx and hypopharynx posterior to the bite block 1. However, the present invention is not limited to such a positioning of the grooves 13 and 14 and other routes for suctioning may be used. For example, the center portion of the bite block 1, i.e., the area between the non-incisor teeth, may be hollowed out to allow passage of a suction catheter. Alternatively, a channel may be cut from the anterior and lateral portion of the bite block exiting in a more medial and posterior area.

Figure 8:
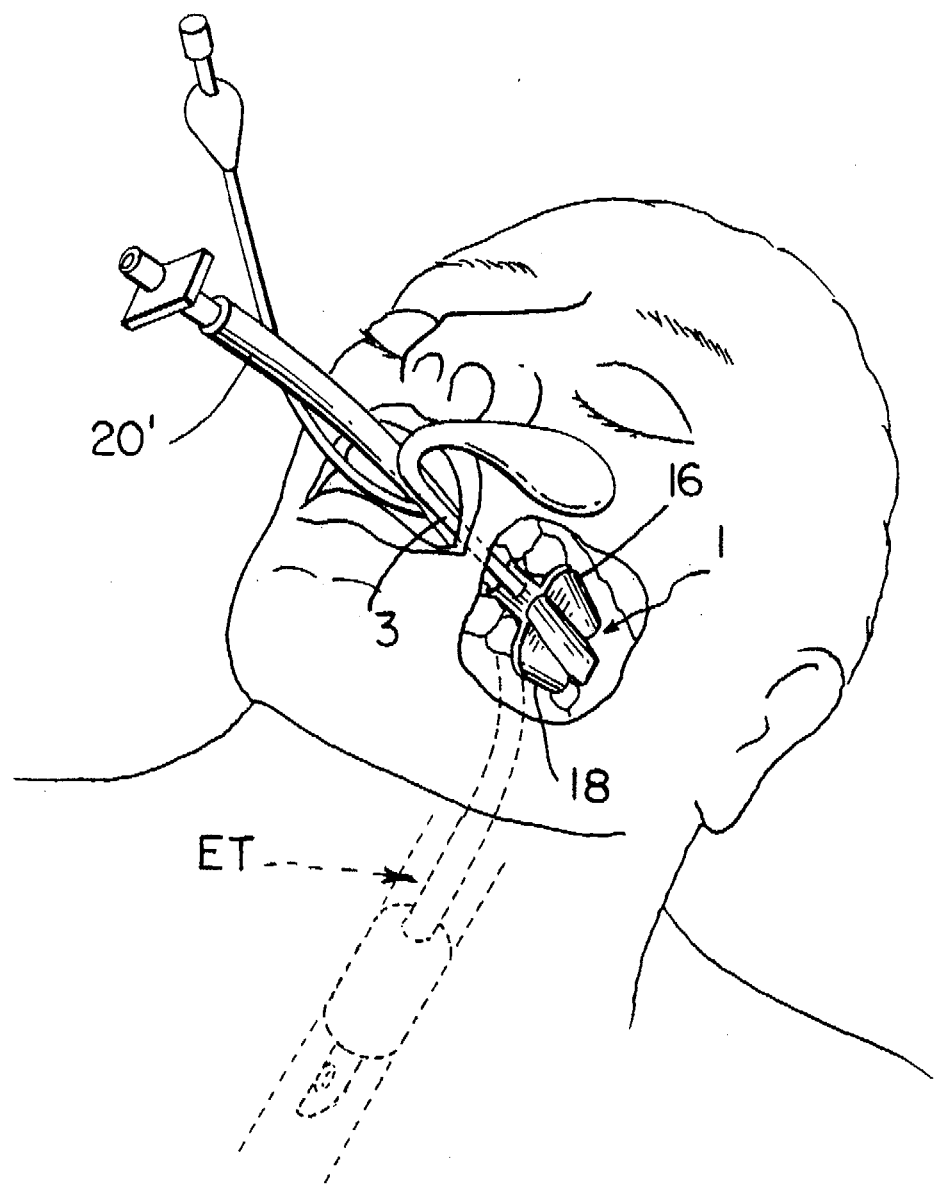
FIG. 8 is a schematic drawing showing the bite block according to the present invention used together with an oral endotracheal tube.

The handle 3 is attached to the bite block portion 2 of the bite block 1 and is used to seat the bite block 1 in a proper position within the patient's mouth, and it also serves to remove the bite block 1 when the bite block is no longer required. In the preferred embodiment, the handle 3 is attached to the central portion of the bite block portion 2 in any conventional manner such as a threaded portion which screws into the bite block portion, or using an adhesive. The handle 3 and bite block portion 2 could be formed as a single piece from, e.g., plastic. Alternatively, the handle 3 could be attached to a more lateral or a more medial portion of the bite block. The handle 3 is preferably made in such a way (round, C-shaped, etc.) as to provide strength as well as to minimize the space which it occupies. As shown in FIGS. 7 and 8, the handle 3 exits the patient's mouth and flattens out and bends away from the mid-line of the mouth. The distal flattened portion 19 of the handle is the portion which the practitioner holds as the bite block 1 is inserted and removed from the patient's mouth. Bending the handle away from the mid-line of the patient's mouth keeps the bite block 1 away from the exiting tube portion 20 of the LMA as is best seen in FIG. 7. While the handle 3 in the preferred embodiment is shown bending away from the mid-line of the patient's mouth, the handle 3 could likewise exit either in a straight-away fashion or towards the mid-line thereby providing a way to bring it in proximity with the exiting or breathing tube 20 of the LMA to permit attachment of the bite block 1 to the corresponding portion of the LMA if desired.

Figure 5:
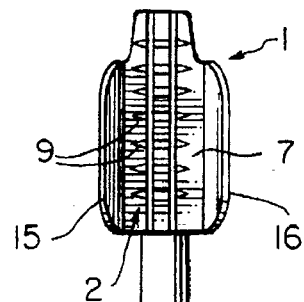
FIG. 5 is a top view of the bite block showing an alternative handle embodiment according to the present invention.

While FIGS. 1 and 4 show the distal flattened portion 19 of the handle 3 shaped and molded so that a thumb and finger can grip it in a comfortable manner, serrations 21 can also be formed on the distal flattened portion 19' as shown in the alternative handle 3' embodiment of FIG. 5 to facilitate gripping. Of course, other shapes and gripping means can be utilized. For example, the handle may have an opening to place a thumb or forefinger through the opening to facilitate stabilization of the product during insertion and removal from the patient's mouth. Alternatively, a scooped-out or thinned-out portion of the distal end of the handle may be utilized to permit the practitioner to better grip the handle. On the surface of the handle, a number, which corresponds to the size of the LMA for which the bite block is intended to be used, may be molded or stamped. Moreover, a device or means to facilitate securing the bite block to the skin of the face may be affixed to the handle.

As best shown in FIG. 3 which illustrates the bite block turned on its side, the bite block 1 is designed to be identical on the upper and lower surfaces (i.e., symmetrical with respect to a horizontal mid-plane which corresponds to a vertical line passing through the handle 3 in FIG. 3) so that it can be rotated 180°. By comprising a mirror image on either side, the bite block can be turned and placed in either side of the mouth. This is a specific and intended advantage of the product which allows the practitioner to decide which side of the patient's mouth to place the bite block based upon such factors as the handedness of the anesthetist, condition of the molars or non-incisor teeth on either side of the mouth, and personal preference of the anesthetist.

Figure 6:
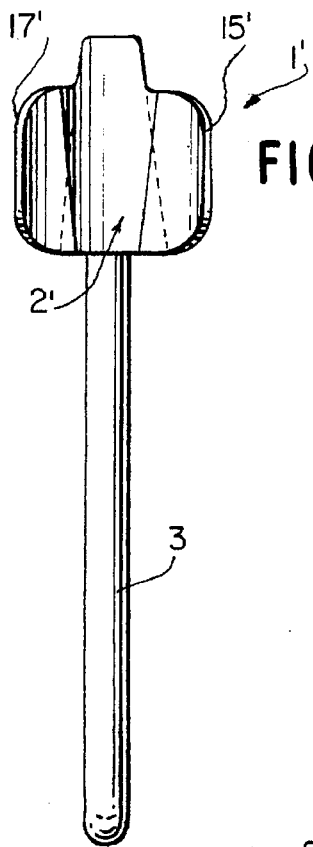
FIG. 6 is a side elevational view of an alternative bite block configuration.

While the flanges 15–18 of the embodiment of FIGS. 1–4 follow the angle of the wedge-shaped bite block portion 2 so as to gradually taper downwardly toward the posterior portion 4 (see especially FIG. 2), the flanges may be formed without any taper as shown in FIG. 6 where the upper medial flange 15' and the lower medial flange 17' are visible.

In use, after general anesthesia has been induced in the patient, the bite block 1 is placed between the non-incisor teeth, such as the molars, and functions to keep the patient's incisors apart. The bite block may be placed either after the LMA has been inserted or, if desired, can be inserted with the intention of stabilizing the jaws with the teeth well separated during insertion of the LMA. FIG. 7 shows the bite block in place between the patient's molars along with the corresponding LMA. Utilizing the bite block of the present invention during insertion of the LMA would be carried out when a practitioner has difficulty in inserting the LMA, or if the practitioner wishes to utilize both hands to insert the LMA rather than utilizing one of his hands to hold the patient's jaws apart. Further, using the handle 3 of the bite block during insertion (or removal) eliminates the chance of the patient biting a practitioner's fingers during light stages of general anesthesia. The presence of the handle 3 also prevents the bite block 1 from slipping into the hypopharynx and causing airway obstruction. During an operation and prior to awakening of the patient from general anesthesia, the practitioner uses the suction channels or grooves 13 and 14 to suction secretion from the posterior oropharynx and hypopharynx. The bite block 1 may be removed either concomitant with the removal of the LMA or shortly before or after the LMA is removed.

Alternatively, as shown in FIG. 8 the bite block 1 can be used with oral endotracheal tubes (ETs) having an exiting tube 20' in patient's where the use of oral airways is normally inadvisable. For example, the use of oral airways in patient's with frontal bridge work or loose incisors can be hazardous and may result in damage to those structures.

The patient airway bite block according to my invention includes the following advantages:

1) The non-incisor teeth engagement surfaces are angled specifically to keep a patient's incisors wide enough apart that they do not impinge upon the breathing portion of the LMA tube (or endotracheal tube).

2) The bite block is made specifically for corresponding LMAs and is sized accordingly. Additionally, the bite block can be made specifically for use with oral endotracheal tubes which have a similar caliber as the tube used for LMAs in any individual patient.

3) The non-incisor teeth engaging surfaces of the bite block are serrated and irregular, or pliable, to provide appropriate gripping and seating of the non-incisor teeth, such as the molars.

4) The upper and lower lateral flanges extending from the bite block portion function to prevent the bite block from moving medially towards the tongue, and prevent the molars from bitting into the mucosa of the cheek.

5) The upper and lower medial flanges prevent the bite block from moving laterally and serve to protect the tongue from being bitten between the bite block and the non-incisor teeth.

6) The free ends of all of the flanges are angled away from the non-incisor teeth in order to keep pressure off the gums and alveolar surfaces and thereby prevent trauma to the oral structures.

7) The handle is an integral portion of the device and is used for insertion and removal of the bite block.

8) The handle prevents the inadvertent loss of the bite block into the posterior oropharynx and hypopharynx.

9) The handle may be curved away from the tube portion of the LMA and thus does not interfere with the appropriate positioning or placement of the LMA.

10) The handle may be flattened to minimize its size and facilitate better gripping by the practitioner.

11) Grooves or serrations may be formed on the flat portion of the handle to further facilitate gripping.

12) A size indicia may be formed in the handle of the bite block which corresponds to the size of the LMA for which the particular block is intended to be used.

13) Grooves or channels may be formed on the medial and lateral side wall portions of the bite block portion to allow suctioning of the posterior airway.

14) The upper and lower portions of the product are mirror images of each other and thereby permit the bite block to be rotated 180° and inserted on either side of the mouth.

It is contemplated that numerous modifications may be made to the patient airway bite block of my invention without departing from the spirit and scope of the invention as defined in the following claims.

What is claimed is:

1. A bite block for use by a human patient, comprising:
   a) a bite block portion defining a posterior portion and an anterior portion and having upper and lower non-incisor teeth engagement surfaces for engaging the patient's upper and lower non-incisor teeth in either side of the patient's mouth, thereby to hold the patient's incisors apart when said bite block is positioned in the patient's mouth at one side thereof;
   b) upper and lower lateral flanges extending from said bite block portion a sufficient distance beyond the biting surface of the non-incisor teeth when said bite block is positioned in the patient's mouth thereby to prevent the bite block from moving medially toward the patient's tongue;
   c) upper and lower medial flanges spaced apart from said upper and lower lateral flanges, respectively, and extending from said bite block portion a sufficient distance beyond the biting surface of the non-incisor teeth when said bite block is positioned in the patient's mouth thereby to prevent said bite block from moving laterally toward the patient's cheek; and d) a stiff handle, for positioning said bite block within the patient's mouth and for removing said bite block therefrom, fixedly attached to said bite block portion and operative to extend outside of the patent's mouth when said bite block is positioned in the patient's mouth.

2. The bite block according to claim 1, wherein said upper and lower non-incisor teeth engagement surfaces are serrated and irregular to provide gripping and seating of the patient's non-incisor teeth.

3. The bite block according to claim 1, wherein said upper and lower non-incisor teeth engagement surfaces are pliable to provide gripping and seating of the patient's non-incisor teeth.

4. The bite block according to claim 1, wherein said bite block portion is wedge-shaped such that said non-incisor teeth engagement surfaces are angled so as to gradually become farther apart in a direction from the posterior portion toward the anterior portion.

5. The bite block according to claim 1, wherein each of said upper and lower lateral flanges and upper and lower medial flanges has a free end which is angled away from the patient's non-incisor teeth.

6. The bite block according to claim 1, wherein said handle has a distal, flattened portion which bends away from a mid-line of the patient's mouth.

7. The bite block according to claim 6, wherein said distal, flattened portion of said handle is serrated for gripping.

8. The bite block according to claim 1, wherein said bite block portion further comprises opposite side walls, each of said side walls having a groove formed therein approximately at the midpoint between the corresponding upper and lower flanges.

9. The bite block according to claim 1, wherein said bite block portion further comprises a projection on the posterior portion which extends beyond said upper and lower lateral and medial flanges and which serves to prevent the bite block from moving too far back in the patient's mouth.

10. The bite block according to claim 1, wherein said bite block is symmetrical about a horizontal mid-plane passing through said bite block portion at a location between said upper and lower lateral and medial flanges.

11. A disposable bite block for use by a human patient, comprising:

a) a bite block portion which is wedge-shaped and defines a posterior portion and an anterior portion and has upper and lower non-incisor teeth engagement surfaces, said wedge-shaped bite block portion being angled such that said non-incisor teeth engagement surfaces gradually become farther apart in a direction from the posterior portion toward the anterior portion, thereby to hold the patient's incisors apart when said bite block is positioned in the patient's mouth at one side thereof;

b) at least one pair of spaced apart flanges extending from said bite block portion and dimensioned to be positioned between the patient's non-incisor teeth and cheek and on the tongue side of the patient's non-incisor teeth, respectively, said at least one pair of spaced apart flanges extending a sufficient distance beyond the biting surface of the non-incisor teeth when said bite block is positioned in the patient's mouth thereby to retain said bite block in place in the patient's mouth; and c) a stiff handle, for positioning said bite block within the patient's mouth and for removing said bite block therefrom, fixedly attached to said bite block portion and operative to extend outside of the patient's mouth when said bite block is positioned in the patient's mouth.

12. The disposable bite block according to claim 11, wherein said upper and lower non-incisor teeth engagement surfaces are serrated and irregular to provide gripping and seating of the patient's non-incisor teeth.

13. The disposable bite block according to claim 11, wherein said upper and lower non-incisor teeth engagement surfaces are pliable to provide gripping and seating of the patient's non-incisor teeth.

14. The disposable bite block according to claim 11, wherein each of said flanges has a free end which is angled away from the patient's non-incisor teeth.

15. The disposable bite block according to claim 11, wherein said handle has a distal, flattened portion which bends away from a mid-line of the patient's mouth.

16. The disposable bite block according to claim 15, wherein said distal, flattened portion of said handle is serrated for gripping.

17. The disposable bite block according to claim 11, wherein said bite block portion further comprises opposite side walls, each of said side walls having a groove formed therein.

18. The disposable bite block according to claim 11, wherein said bite block portion further comprises a projection on the posterior portion which extends beyond said flanges and which serves to prevent the bite block from moving too far back in the patient's mouth.

19. The disposable bite block according to claim 11, wherein said bite block is symmetrical about a horizontal mid-plane passing through said bite block portion between said upper and lower non-incisor teeth engagement surfaces.

20. A patient airway bite block for use with a patient airway including one of a laryngeal mask airway and an oral endotracheal tube, the patient airway having an exiting tube portion positioned in the mid-line of a patient's mouth, said patient airway bite block comprising:

a) a bite block portion which is wedge-shaped and defines a posterior portion and an anterior portion and has upper and lower non-incisor teeth engagement surfaces, said wedge-shaped bite block portion being angled such that said non-incisor teeth engagement surfaces gradually become farther apart in a direction from the posterior portion toward the anterior portion, thereby to hold the patient's incisors apart when said bite block is positioned in the patient's mouth at one side thereof and thus prevent the patient from biting down on the exiting tube portion of the patient airway;

b) at least one pair of spaced apart flanges extending from said bite block portion and dimensioned to be positioned between the patient's non-incisor teeth and cheek and on the tongue side of the patient's non-incisor teeth, respectively, said at least one pair of spaced apart flanges extending a sufficient distance beyond the biting surface of the non-incisor teeth when said bite block is positioned in the patient's mouth thereby to retain said bite block in place in the patient's mouth; and c) a handle, for positioning said bite block within the patient's mouth and for removing said bite block therefrom, fixedly attached to said bite block portion and operative to extend outside of the patient's mouth when said bite block is positioned in the patient's mouth.

21. The patient airway bite block according to claim 20, wherein said bite block is formed from plastic.

22. The patient airway bite block according to claim 20, wherein said bite block is disposable.

23. The patient airway bite block according to claim 20, further comprising another pair of spaced apart flanges, wherein said one pair of spaced apart flanges are upper flanges and the other pair of spaced apart flanges are lower flanges.

24. The patient airway bite block according to claim 20, wherein said upper and lower non-incisor teeth engagement surfaces are serrated and irregular to provide gripping and seating of the patient's non-incisor teeth.

25. The patient airway bite block according to claim 20, wherein said upper and lower non-incisor teeth engagement surfaces are pliable to provide gripping and seating of the patient's non-incisor teeth.

26. The patient airway bite block according to claim 20, wherein each of said flanges has a free end which is angled away from the patient's non-incisor teeth.

27. The patient airway bite block according to claim 20, wherein said handle has a distal, flattened portion which bends away from a mid-line of the patient's mouth and in turn away from the exiting tube portion.

28. The patient airway bite block according to claim 27, wherein said distal, flattened portion of said handle is serrated for gripping.

29. The patient airway bite block according to claim 20, wherein said bite block portion further comprises opposite side walls, each of said side walls having a groove formed therein for permitting passage of a suction catheter.

30. The patient airway bite block according to claim 20, wherein said bite block portion further comprises a projection on the posterior portion which extends beyond said flanges and which serves to prevent the bite block from moving too far back in the patient's mouth.

31. The patient airway bite block according to claim 23, wherein said bite block is symmetrical about a horizontal mid-plane passing through said bite block portion at a location between said upper and lower flanges.

32. The patient airway bite block according to claim 23, wherein the upper and lower flanges are angled inwardly toward said bite block portion in a direction toward the posterior portion.

33. The patient airway bite block according to claim 23, wherein the upper and lower flanges protrude from said bite block portion without any taper.

* * * * *